(12) United States Patent
Hanson et al.

(10) Patent No.: US 10,434,284 B2
(45) Date of Patent: Oct. 8, 2019

(54) MEDICAL DRESSING COMPRISING A FLAP

(71) Applicant: 3M INNOVATIVE PROPERTIES COMPANY, St. Paul, MN (US)

(72) Inventors: Jennifer N. Hanson, St. Paul, MN (US); Donald G. Peterson, Shoreview, MN (US); Michael D. Determan, Mahtomedi, MN (US); Matthew H. Fryxell, Minnetonka, MN (US); Joseph M. Hommes, St. Paul, MN (US); Michael R. Plumb, White Bear Lake, MN (US); Anila Prabhu, Woodbury, MN (US); Kiu-Yuen Tse, Woodbury, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 792 days.

(21) Appl. No.: 14/652,152

(22) PCT Filed: Dec. 16, 2013

(86) PCT No.: PCT/US2013/075252
§ 371 (c)(1),
(2) Date: Jun. 15, 2015

(87) PCT Pub. No.: WO2014/099709
PCT Pub. Date: Jun. 26, 2014

(65) Prior Publication Data
US 2016/0193452 A1 Jul. 7, 2016

Related U.S. Application Data

(60) Provisional application No. 61/783,582, filed on Mar. 14, 2013, provisional application No. 61/740,778, filed on Dec. 21, 2012.

(51) Int. Cl.
*A61F 13/00* (2006.01)
*A61M 25/02* (2006.01)
*A61F 13/02* (2006.01)

(52) U.S. Cl.
CPC .......... *A61M 25/02* (2013.01); *A61F 13/025* (2013.01); *A61F 13/0253* (2013.01); *A61M 2025/0266* (2013.01); *A61M 2025/0273* (2013.01)

(58) Field of Classification Search
USPC .................................................. 604/179, 180
See application file for complete search history.

(56) References Cited

U.S. PATENT DOCUMENTS 2,464,662 A   3/1949   Young
RE24,906 E   12/1960   Ulrich
(Continued)

FOREIGN PATENT DOCUMENTS

CN   2015-43039   8/2010
EP   1350534   10/2003
(Continued)

OTHER PUBLICATIONS

International Search Report for PCT International Application No. PCT/US2013/075252 dated Apr. 23, 2014, 5 pages.

*Primary Examiner* — Kim M Lewis
(74) *Attorney, Agent, or Firm* — 3M Innovative Properties Company; Trisha D. Adamson

(57) ABSTRACT

A medical dressing (100) with a dressing body (102) and a flap (104). The flap can include a fixed end (120) coupled to the dressing body, and a free end (122) movable with respect to the dressing body between a first position and a second position in which the free end is positioned in overlapping relationship with the dressing body. A second major surface (116) of at least the free end of the flap can be configured to be secured to the dressing body, and the flap can be located (Continued)

toward a proximal end of the dressing body, such that a distal portion of the dressing body is free of the flap. The dressing body can be adhered to skin with a skin-contact adhesive (e.g., a silicone adhesive) (115), and the flap can be secured to the dressing body with a securing adhesive (e.g. an acrylate adhesive) (117) that can have a higher adhesion or adhesive strength.

12 Claims, 8 Drawing Sheets

(56) References Cited

U.S. PATENT DOCUMENTS

| | | | |
|---|---|---|---|
| 3,389,827 A | 6/1968 | Abere | |
| 3,645,835 A | 2/1972 | Hodgson | |
| 3,826,254 A * | 7/1974 | Mellor | A61M 25/02 128/DIG. 26 |
| 4,059,105 A | 11/1977 | Cutruzzula | |
| 4,112,213 A | 9/1978 | Waldman | |
| 4,310,509 A | 1/1982 | Berglund | |
| 4,323,557 A | 4/1982 | Rosso | |
| 4,399,816 A * | 8/1983 | Spangler | A61F 13/0206 128/888 |
| 4,499,896 A | 2/1985 | Heinecke | |
| 4,583,976 A | 4/1986 | Ferguson | |
| 4,595,001 A | 6/1986 | Potter | |
| 4,702,736 A | 10/1987 | Kalt | |
| 4,737,410 A | 4/1988 | Kantner | |
| 4,822,342 A * | 4/1989 | Brawner | A61M 25/02 128/DIG. 26 |
| 4,882,377 A | 11/1989 | Sweet | |
| 5,147,322 A | 9/1992 | Bowen | |
| 5,266,401 A | 11/1993 | Tollini | |
| 5,282,791 A | 2/1994 | Lipton | |
| 5,304,146 A | 4/1994 | Johnson | |
| 5,531,855 A | 7/1996 | Heinecke | |
| 6,015,119 A | 1/2000 | Starchevich | |
| 6,043,408 A * | 3/2000 | Geng | A61F 13/023 602/54 |
| 6,103,369 A | 8/2000 | Lucast | |
| 6,264,976 B1 | 7/2001 | Heinecke | |
| 6,311,933 B1 | 11/2001 | Starchevich | |
| 7,624,480 B2 | 12/2009 | Coronel | |
| 7,985,206 B2 | 7/2011 | Dikeman | |
| 8,251,957 B2 | 8/2012 | Kyvik | |
| 2003/0055382 A1 | 3/2003 | Schaeffer | |
| 2005/0215953 A1 | 9/2005 | Rossen | |
| 2007/0073211 A1 | 3/2007 | Propp | |
| 2008/0065022 A1 | 3/2008 | Kyvik | |
| 2008/0171958 A1 * | 7/2008 | Gundersen | A61F 13/0206 602/56 |
| 2008/0200880 A1 * | 8/2008 | Kyvik | A61M 25/02 604/180 |
| 2008/0233348 A1 | 9/2008 | Ishiwatari | |
| 2009/0259188 A1 | 10/2009 | Bierman | |
| 2010/0159192 A1 | 6/2010 | Cotton | |
| 2011/0021997 A1 * | 1/2011 | Kyvik | A61M 25/02 604/180 |
| 2011/0202010 A1 | 8/2011 | Bierman | |
| 2011/0212325 A1 | 9/2011 | Determan | |
| 2012/0083743 A1 | 4/2012 | kyvik | |
| 2012/0109070 A1 | 5/2012 | Elsamahy | |

FOREIGN PATENT DOCUMENTS

| | | |
|---|---|---|
| EP | 1350535 | 10/2003 |
| GB | 2451726 | 2/2009 |
| GB | 2464662 | 4/2010 |
| JP | 49-139360 | 4/1948 |
| JP | S5244301 | 4/1977 |
| JP | 2009017941 | 1/2009 |
| WO | WO 1995-24238 | 9/1995 |
| WO | WO 2006-074700 | 7/2006 |
| WO | WO 2010-039751 | 4/2010 |
| WO | WO 2010-056541 | 5/2010 |
| WO | WO 2010-056543 | 5/2010 |
| WO | WO 2010-056544 | 5/2010 |
| WO | WO 2011-025478 | 3/2011 |
| WO | WO 2014-014504 | 1/2014 |
| WO | WO 2014-099709 | 6/2014 |
| WO | WO 2015-0020875 | 2/2015 |

* cited by examiner

MEDICAL DRESSING COMPRISING A FLAP

CROSS REFERENCE TO RELATED APPLICATIONS

This is a national stage filing under 35 U.S.C. § 371 of PCT/US2013/075252, filed Dec. 16, 2013, which claims priority to U.S. Provisional Application Nos. 61/783,582, filed Mar. 14, 2013 and 61/740,778, filed Dec. 21, 2012, the disclosures of which are incorporated herein by reference in their entirety.

FIELD

The present disclosure relates to a medical dressing comprising a flap. In particular, the present disclosure relates to a medical dressing for safely and reliably securing a medical article, such as a catheter system, upon a desired location of a patient's body.

BACKGROUND

Medical adhesive dressings are used for a variety of medical applications, such as for securing medical devices to skin. Adhesive dressings can provide barrier protection from infectious species to a wound or catheter insertion site. Transparent adhesive dressings are commonly used at a catheter insertion site because visual monitoring of the site can be achieved without removing the dressing. Poor or weak securement of an inserted medical device can increase the risk for potential infiltration of antagonistic microbes which can result in the need for device reinsertion or can lead to complications such as phlebitis and catheter related bloodstream infections (CRBSIs). When a patient experiences a CRBSI, mortality and morbidity rates increase significantly. Because loss of a catheter line or other medical device can be so devastating for the patient, adhesives which have strong adhesion to the skin are often used to secure such devices; these adhesives, however, can be very damaging to skin when removed. Use of a more gentle adhesive can significantly reduce skin damage such as edema, erythema, and skin stripping or tearing. Common gentle adhesives (e.g., silicone-based adhesives), however, typically have poor adhesion to the inserted medical devices and/or tubing.

SUMMARY

The present disclosure generally relates to medical dressing comprising a flap (e.g., a tape flap) for safely and reliably securing a medical article, such as a catheter system, upon a desired location of a patient's body. In general, the medical dressing can include a dressing body that adheres to the patient's skin, and a flap having a fixed end coupled to the dressing body that secures at least a portion of the medical article, e.g., in some embodiments, with a more aggressive adhesive than what is used to secure the dressing body to the skin.

Some aspects of the present disclosure provide a medical dressing, e.g., for securing a medical article to a skin surface. The medical dressing can include a dressing body comprising a first major surface, and a second major surface, opposite the first major surface, comprising a skin-contact adhesive. The medical dressing can further include a flap comprising a first major surface; a second major surface, opposite the first major surface; a fixed end coupled to the dressing body; and a free end movable with respect to the dressing body between a first position in which the free end is not positioned in an overlapping relationship with the dressing body and a second position in which the free end is positioned in overlapping relationship with the dressing body. The second major surface of at least the free end of the flap can be configured to be secured to the dressing body, and the flap can be located toward a proximal end of the dressing body, such that a distal portion of the dressing body is free of the flap.

Some aspects of the present disclosure provide a medical dressing. The medical dressing can include a dressing body comprising a first major surface, and a second major surface, opposite the first major surface. At least a portion of the second major surface can include a silicone adhesive. The medical dressing can further include a flap comprising a first major surface; a second major surface, opposite the first major surface; a fixed end coupled to the dressing body; and a free end movable with respect to the dressing body between an open position in which the free end is not positioned in an overlapping relationship with the dressing body and a second position in which the free end is positioned in overlapping relationship with the dressing body. At least the free end of the flap can be configured to be secured to the dressing body by an acrylate adhesive when the free end of the flap is in the second position.

Other features and aspects of the present disclosure will become apparent by consideration of the detailed description and accompanying drawings.

DETAILED DESCRIPTION

Figure 1:
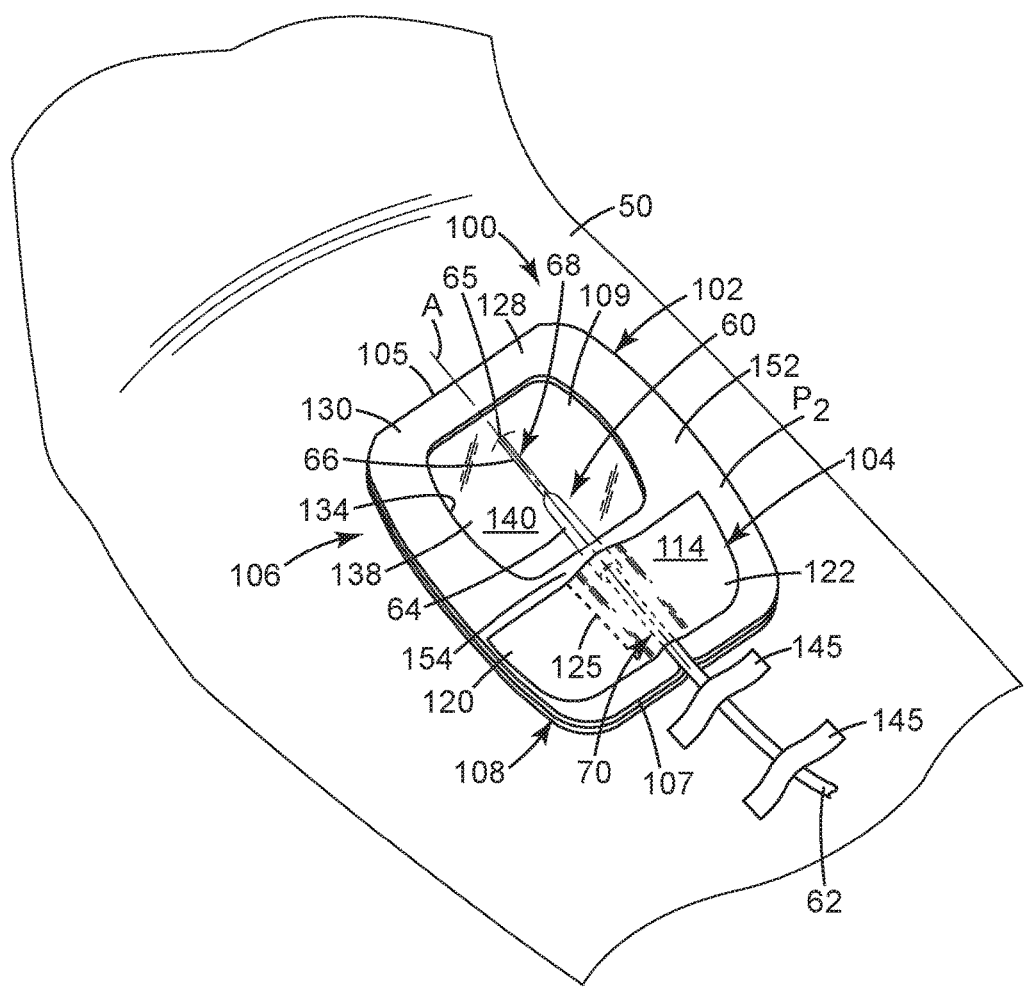
FIG. 1 is a perspective view of a medical dressing according to one embodiment of the present disclosure, showing the medical dressing being used to couple a medical article to a patient.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof are used broadly and encompass both direct and indirect couplings. It is to be understood that other embodiments may be utilized and structural or logical changes may be made without departing from the scope of the present disclosure. Furthermore, terms such as "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to medical dressing comprising a flap for safely and reliably securing a medical article, such as a catheter system, upon a desired location of a patient's body. The medical dressing can include a dressing body that includes a less aggressive adhesive for adhering to skin and a flap that has a fixed end coupled to the dressing body and that includes a more aggressive adhesive for reliably securing at least a portion of the medical article, for example, by adhering to a top surface of the dressing body rather than the skin.

The medical dressings of the present disclosure can be universal to accommodate and reliably secure a large variety of medical articles or class of medical articles (e.g., PICCs, CVCs, Inserted Ports, PIVs, etc.), and can be particularly useful for securing medical articles that need to be secured to a patient over a prolonged period of time, such as weeks or months.

Examples of medical articles that can be employed with the medical dressings of the present disclosure include, but are not limited to, connector fittings, catheter systems (e.g., including catheters, catheter hubs, catheter adaptors, etc.), fluid supply lines, inserted ports, other similar articles, or combinations thereof. Examples of catheter systems can include, but are not limited to, intravenous (IV) catheters (e.g., peripheral intravenous catheters PIVs), central venous catheters (CVCs), peripherally inserted central catheters (PICCs), arterial catheters, urinary catheters, and dialysis catheters.

The terms "longitudinal" and "axial" are used to refer to a direction or axis that is generally parallel to the direction in which the medical article extends and generally parallel to the overall direction of fluid flow, e.g., along a catheter line.

The term "lateral" or "transverse" is used to refer to a direction or axis that is perpendicular to the longitudinal axis or direction and is used to represent side-to-side motion of a medical article.

The terms "vertical" and "normal" are used to refer to a direction or axis that is normal to both the longitudinal and lateral directions or axes, as well as to the surface of a patient's skin when the medical dressing is coupled to the patient's skin, and is used to represent the direction of motion toward and away from the skin surface.

The term "proximal" and "distal" are used to represent axial directions, relative to a medical practitioner operating or holding the medical article. That is, the term "distal" is used to refer to the direction away from the medical practitioner (and toward an insertion site on the patient and inside the patient's body), and the term "proximal" is used to refer to the direction toward the medical practitioner (and toward the outside of the patient's body, away from the insertion site). For example, the distal end of a catheter is inserted into the patient, while the proximal end extends exterior of the patient toward the medical practitioner. The distal end of the medical dressing refers to the end of the medical dressing that is configured to be oriented toward the distal end of the medical article to which it will be coupled, and the proximal end of the medical dressing refers to the end of the medical dressing that is configured to be oriented toward the proximal end of the medical article. As a result, in the case of catheter systems, the distal end of the medical dressing will be oriented toward the insertion site on the patient's body, and the proximal end of the of the medical dressing will be oriented away from the insertion site on the patient's body.

Figure 2:
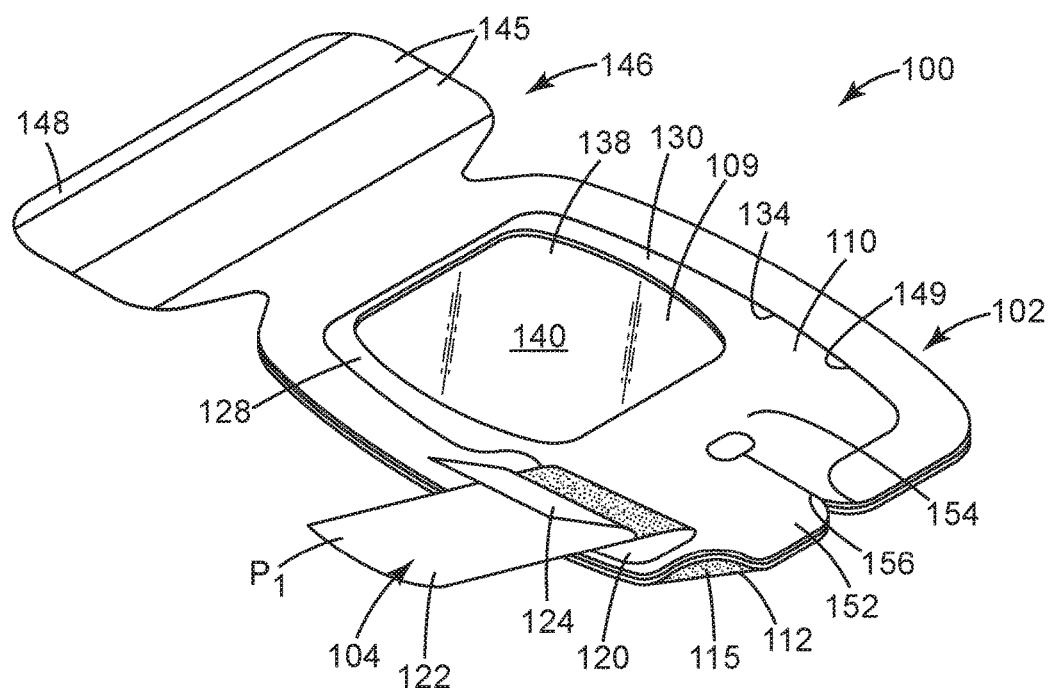
FIG. 2 is a perspective view of the medical dressing of FIG. 1, with release liners and a frame.

FIGS. 1-6 illustrate a medical dressing 100 according to one embodiment of the present disclosure. FIG. 1 illustrates a medical dressing 100 coupled to the skin 50 of a patient, and particularly, to an arm of the patient. FIG. 1 also illustrates an exemplary medical article 60 coupled to the medical dressing 100. By way of example only, the medical article 60 is illustrated as being a catheter system which can include one or more input catheters (or tubes or lines) 62, a catheter hub 64, and one or more output catheters (or tubes or lines) 66. FIG. 2 shows the medical dressing 100 prior to coupling the medical dressing 100 to the patient.

As shown, the medical article 60 can have a longitudinal axis A that extends along and defines a longitudinal direction. The medical article can extend distally to include a first longitudinal, distal end or portion 68 (which may extend beyond what is shown in FIG. 1, e.g., into an interior of the patient's body), and can extend proximally to include a second longitudinal, proximal end or portion 70 (which may extend further proximally and include additional elements than what is shown in FIG. 1).

By way of example only, the distal portion 68 of the medical article 60 is shown as entering a peripheral vein in a patient's arm at an insertion site 65, and the proximal portion 70 is shown to include one input catheter 62, which can terminate at a connector (not shown). Such a connector can be connected to a fluid supply line, or the like, for delivery of a variety of nutrients or medicaments to the patient.

As shown, the medical dressing 100 can include a dressing body 102 and a flap 104. The dressing body 102 can include a first major surface (e.g., a top major surface) 110 configured to face away from the patient's skin 50, and a second major surface (e.g., a bottom major surface) 112 opposite the first major surface 110 that comprises a skin-contact adhesive 115 (see FIGS. 2 and 6) for adhering to the skin 50. The dressing body 102 can include a distal end 105 and a proximal end 107, and accordingly, a distal portion 106 located toward the distal end 105, and a proximal portion 108 located toward the proximal end 107. As shown, in some embodiments, the distal portion 106 of the dressing body 102 can include a transparent window 109 that can be located over a portion (e.g., the distal portion 68) of the medical article 60 and/or the patient's skin 50 that is desired to be monitored while the medical dressing 100 is coupled to the patient without having to remove the medical dressing 100.

The flap 104 can include a first major surface (e.g., a top major surface) 114 and a second major surface (e.g., a bottom major surface) 116, opposite the first major surface 114. The second major surface 116 can include a securing adhesive 117 for securing at least a portion of the medical article 60, for example, to the first major surface 110 of the dressing body 102. The flap 104 can further include a fixed end 120 coupled to the dressing body 102 and a free end 122 movable with respect to the dressing body 102 between a first (i.e., open) position $P_1$ (see FIGS. 2-4) in which the free end 122 is not positioned in an overlapping relationship with the dressing body 102 and a second (i.e., closed) position $P_2$ (see FIGS. 1, 5 and 6) in which the free end 122 is positioned in overlapping relationship with the dressing body 102.

The securing adhesive 117 is shown and described by way of example only, but it should be understood that in any of the embodiments described and illustrated herein, the flap 104 can instead be secured to the dressing body 102 using another type of fastener or fastener system, such as a mechanical fastener. A mechanical fastener can include, but is not limited to, a hook-and-loop fastener, a hook-and-stem fastener, a hook-and-hook fastener, a stem-and-stem fastener, or the like, or combinations thereof. Still, other types of fasteners can be employed in medical dressings of the present disclosure. In some embodiments, a securing adhesive can be a preferred means for fastening at least the free end 122 of the flap 104 to the dressing body 102, e.g., for hygiene and sanitation purposes.

As shown, at least a portion of the second major surface 116 of at least the free end 122 of the flap 104 can be configured to be secured to the dressing body 102 (i.e., to the first major surface 110 of the dressing body 102) by the securing adhesive 117, i.e., when the free end 122 of the flap 104 is in the second position $P_2$. As shown, the flap 104 can be located toward or adjacent the proximal end 107 of the dressing body 102 and can be configured to overlap the proximal portion 108 of the dressing body 102, such that the distal portion 106 of the dressing body 102 is free of the flap 104. Such a configuration can be important particularly in embodiments of the medical dressing 100 employing the transparent window 109, for example, so that the flap 104 is located proximally with respect to the transparent window 109 and does not interfere with visually monitoring at least a portion of the medical article 60 and/or the patient, such as the insertion site 65 if a catheter system is employed.

As shown in FIG. 1, the flap 104 can be particularly suitable for securing the medical article 60 adjacent the first major surface 110 of the dressing body 102, for example, from undesired longitudinal, lateral and/or vertical movement while the medical article 60 is coupled to the patient. As such, the dressing body 102 can secure the distal portion 68 of the medical article 60, and the flap 104 can function with the dressing body 102 to further secure the proximal portion 70 of the medical article 60.

Although only a single shape of the dressing body 102 is illustrated, it should be understood that the dressing body 102 can take on a variety of shapes and sizes, depending on the shape and configuration of the medical article 60 to be employed. In some embodiments, as shown, the dressing body 102 can include a laminated structure comprising more than one layer.

By way of example only, in the embodiment of FIGS. 1-6, the dressing body 102 includes a top layer 128 having a first major surface 130 that defines at least a portion of the overall first major surface 110 of the dressing body 102, and a second major surface 132 configured to be coupled to a lower layer of the dressing body 102. For example, in some embodiments, as shown, the second major surface 132 can include a securing adhesive 133 that can have similar properties as the securing adhesive 117 of the flap 104, which is described in greater detail below.

As further shown, in some embodiments, the dressing body 102 can further include a base layer 138 having a first major surface 140 and a second major surface 142 that defines at least a portion of the overall second major surface 112 of the dressing body 102 and can therefore include the skin-contact adhesive 115. Other layers can be employed in the dressing body 102, and the top layer 128 and the base layer 138 are shown by way of example only.

As further shown by way of example only, the base layer 138 is transparent, and the top layer 128 includes an opening 134 formed therethrough, such that the top layer 128 and the base layer 138 together form the transparent window 109. However, it should be understood that other configurations are possible, such as where the base layer 138 is more opaque and includes the opening 134, and the top layer 128 is transparent and forms an overlay liner for the base layer 138. In still other embodiments, the dressing body 102 can include one single layer and can be transparent in the region of the transparent window 109.

In embodiments in which the base layer 138 includes the opening 134 and the top layer 128 is transparent and forms an overlay liner (or film) over the base layer 138, a variety of configurations can be employed. For example, in some embodiments, the top layer 128 can be free of adhesive, and the base layer 138 can include an adhesive on its first major surface 140 and its second major surface 142, such that the portion of the top layer 128 that overlaps the opening 134 (and, e.g., the insertion site 65) is free of adhesive. In such embodiments, the first major surface 140 of the base layer 138 can include a securing adhesive (e.g., an acrylate adhesive), and the second major surface 142 (defining at least a portion of the overall second major surface 112 and being skin-facing) can include the skin-contact adhesive 115 (e.g., a silicone adhesive). Also, in such embodiments, the portion of the top layer 128 overlapping the opening 134 presents no adhesive to the medical article 60 and/or the skin 50 underneath.

Furthermore, in some embodiments in which the base layer 138 includes the opening 134 and the top layer 128 is transparent and forms an overlay liner (or film) over the base layer 138, the second major surface 132 of the top layer 128 can include the securing adhesive 133 (e.g., an acrylate adhesive), and the second major surface 142 of the base layer 138 can include the skin-contact adhesive 115 (e.g., a silicone adhesive). In such embodiments, the portion of the top layer 128 overlapping the opening 134 presents the securing adhesive 133 to the medical article 60 and/or the skin 50 underneath.

Still, in some embodiments in which the base layer 138 includes the opening 134 and the top layer 128 is transparent and forms an overlay liner (or film) over the base layer 138, the second major surface 132 of the top layer 128 can include a skin-contact adhesive (e.g., the skin-contact adhesive 115, e.g., a silicone adhesive), and the second major surface 142 of the base layer 138 can include the skin-contact adhesive 115 (e.g., a silicone adhesive). In such embodiments, the portion of the top layer 128 overlapping the opening 134 presents a skin-contact adhesive to the medical article 60 and/or the skin 50 underneath.

The skin-contact adhesive 115 is generally a pressure-sensitive adhesive, and particularly is a pressure-sensitive adhesive that is capable of securely but releasably adhering or bonding to skin (e.g., mammalian skin). The skin-contact adhesive 115 is also generally safe and non-toxic. Skin-contact adhesive layers will generally be selected according to the desired end use of the dressing body 102. In some embodiments, the dressing body 102 can include more than one skin-contact adhesive 115. Where the dressing body 102 comprises more than one skin-contact adhesive layer 115, each skin-contact adhesive layer 115 may be selected independently of each other with regard to material and thickness used. Examples of suitable skin-contact adhesives are described in greater detail below.

In some embodiments, e.g., in embodiments employing silicone adhesives, the dressing body 102 and the skin-contact adhesive 115 can be perforated to provide openings from the first major surface 110 of the dressing body 102 all the way through the second major surface 112 and the skin-contact adhesive 115, which can enhance permeability of the dressing body 102 and can minimize moisture buildup at the skin surface underlying the dressing body 102.

The medical dressing 100 can further include one or more release liners that can provide a release layer or surface to the skin-contact adhesive 115 on the second major surface 112 of the dressing body 102 prior to use. Examples of liners suitable for use with medical dressings of the present disclosure are described below.

Figure 7:
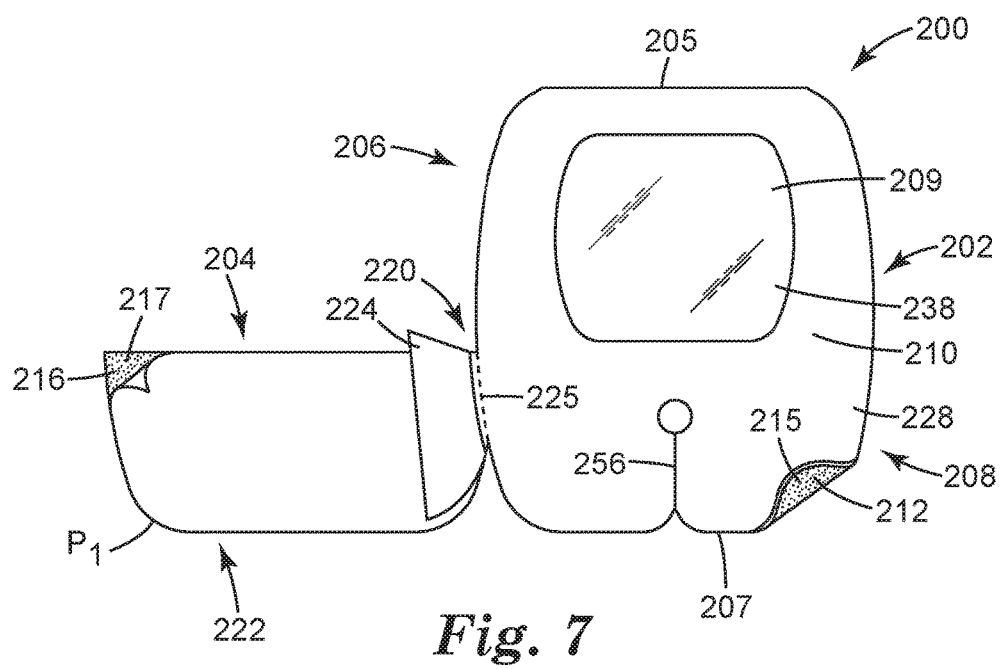
FIG. 7 is a top plan view of a medical dressing according to another embodiment of the present disclosure, shown prior to use.
Figure 8:
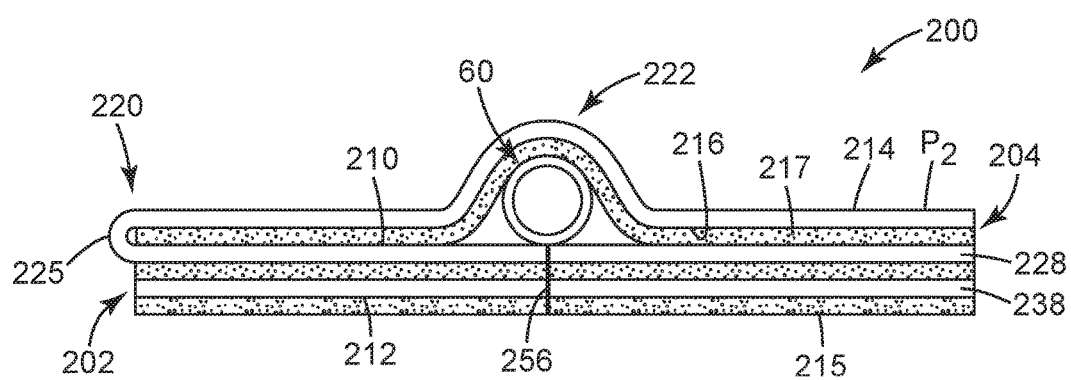
FIG. 8 is an end view of the medical dressing of FIG. 7, shown in use with a medical article.

In some embodiments, as shown in FIGS. 1-6, the fixed end 120 of the flap 104, and particularly, the second major surface 116 of the flap 104 in the area of the fixed end 120, can be adhered or otherwise secured or coupled to the first major surface 110 of the dressing body 102. In other embodiments, for example, as shown in FIGS. 7-8 and described below, the fixed end 120 of the flap 104 can be integrally formed with the dressing body 102, or provided by a portion of the dressing body 102, and separated from the dressing body 102 (or a remainder of the dressing body 102) by a living hinge.

In some embodiments, a low adhesion coating (low adhesion backsize or LAB) may be provided on the first major surface 110 of the dressing body 102 (e.g., on the first major surface 130 of the top layer 128) at least in a region that that comes in contact with the carrier layer 146 and/or the flap 104. The low adhesion coating can reduce the need to change the entire medical dressing 100 (or the dressing body 102) due to unwanted dressing removal when other tapes or devices are placed on the medical dressing 100 (or the dressing body 102) and removed, and can also reduce the surface friction of the medical dressing 100 on linen or other fabrics, thereby offering additional protection against the accidental removal of medical dressing 100. A description of a low adhesion backing material suitable for use with medical dressings of the present disclosure can be found in U.S. Pat. Nos. 5,531,855 and 6,264,976, which are incorporated herein by reference in their entirety.

As shown in FIGS. 1-6, the flap 104 can include the securing adhesive 117 on its second major surface 116 in the area of (or adjacent) the fixed end 120 and the free end 120. A release liner 124 can be employed to cover the securing adhesive 117 on the free end 122 of the flap 104 until it is desired to move free end 122 of the flap 104 into the second position $P_2$ and secure the second major surface 116 of the flap 104 to the dressing body 102 and/or the medical article 60 using the securing adhesive 117. That is, in some embodiments, a first portion of the second major surface 116 of the flap 104 (i.e., adjacent or including the fixed end 120 of the flap 104) can be secured by the securing adhesive 117 to the first major surface 110 of the dressing body 102, and a second portion of the second major surface 116 of the flap 104 (i.e., adjacent or including the free end of the flap) can include the removable release liner 124 covering the securing adhesive 117 prior to use.

In some embodiments, as shown in FIGS. 1-6, the securing adhesive 117 can be continuous along the second major surface 116 of the flap 104, and while the fixed end 120 is adhered to the first major surface 110 of the dressing body 102, the free end 122 can be covered by the release liner 124 prior to use. However, in some embodiments, there can be multiple sections of the securing adhesive 117. For example, in some embodiments, one portion of the securing adhesive 117 can be located adjacent the fixed end 120 of the flap 104 and another portion of the securing adhesive 117 can be located adjacent the free end 122 of the flap 104 in such a way that a middle section of the flap 104 remains free of the securing adhesive 117. In such embodiments, a portion (e.g., the ultimate end) of the free end 122 of the flap 104 can still be adhered to the dressing body 102 when in the second position $P_2$ to provide some security to the medical article secured, but lifting of the flap 104 would not cause unnecessary or painful pulling motions on the secured medical article.

In some embodiments, different securing adhesives can be employed adjacent the fixed end 120 and the free end 122 of the flap 104, and in some embodiments, the same securing adhesive 117 can be employed across the entire second major surface 116 of the flap 104.

In embodiments such as the embodiment of FIGS. 1-6 where the fixed end 120 of the flap 104 is adhered to the first major surface 110 of the dressing body 102, the flap 104 itself can include a living hinge 125 (see FIGS. 1 and 6) about which the free end 122 of the flap 104 can pivot between the first position $P_1$ and the second position $P_2$. By way of example only, the flap 104 can be used to secure a proximal portion of the medical article 60, e.g., proximal with respect to the insertion site 65 in the case where the medical article 60 is a catheter system, and the flap 104 can be used to secure the input catheter 62 to the dressing body 102.

As shown, in some embodiments, the medical dressing 100 can further include one or more auxiliary tape strips 145 that can be used to further secure other portions of the medical article 60 (e.g., more proximal portions of the input catheter 62) to the patient's skin 50. As shown, the auxiliary tape strips 145 can be provided by an optional carrier or frame layer 146 and are not coupled to the dressing body 102, particularly, not in the same way as the flap 104. The auxiliary tape strips 145 are optional and only shown by way of example only.

The carrier layer 146 is optionally positioned over the dressing body 102. The carrier layer 146 can be a single piece of material, such as a polymeric film, or can be two or more distinct pieces. In the embodiment of FIGS. 1-6, the carrier layer 146 comprises at least one portion that extends beyond the edge of the dressing body 102 to form a tab 148. The tab 148 can be held during positioning of the medical dressing 100. The release liner for the medical dressing 100 can also include a tab that corresponds in shape, size and relative position to the tab 148 of the carrier layer 146.

As shown, the carrier layer 146 can extend along at least a portion of the periphery of the dressing body 102 and form a window 149 exposing a portion of the dressing body 102. As such, the carrier layer 146 and its window 149 form a frame extends slightly less than completely around the perimeter of the dressing body 102. The window 149 allows the dressing body 102 to be placed over the medical article 60 while still being attached to the carrier layer 146 to increase the ease of handling of dressing body 102 (or the medical dressing 100 as a whole).

As further shown in FIGS. 1-6, in some embodiments, the dressing body 102 can include a perimeter (or peripheral region) 152 surrounding a central portion 154 of the dressing body 102, and a recess (or slit or notch) 156 extending from the perimeter 152 into a central portion 154 of the dressing body 102, the recess 156 configured to allow a portion (e.g., an elongated member, such as a percutaneous device, e.g., a catheter) of a medical device 60 to pass therethrough. As shown, in some embodiments, the recess 156 can be formed in the proximal portion 108 of the dressing body 102 and can extend through the proximal end 107 of the dressing body 102. For example, the recess 156 can allow the dressing body 102 to conform around bulky parts of the medical article 60, or may conform around portions of the device that exit the area of dressing application, such as a catheter line. By way of example, in embodiments employing a catheter system as the medical article 60, the recess 156 can be configured to allow a portion (e.g., the proximal portion 70) of the medical article 60 (e.g., the input catheter 62 that is proximal relative to the insertion site 65) to pass from the second major surface 112 of the dressing body 102 to the first major surface 110 of the dressing body 102, to allow the portion of the medical article 60 to reside on top of the dressing body 102 when the medical dressing 100 is coupled to the patient. In such cases, the second major surface 112 of the dressing body 102 can still include the skin-contact adhesive 115, such that after the portion of the medical article 60 is passed from the second major surface 112 of the dressing body 102 to the first major surface 110 of the dressing body 102 via the recess 156, the second major surface 112 of the dressing body 102 that is located adjacent (or that defines) the recess 156 can be secured to the skin 50 with the skin-contact adhesive 115.

Such a configuration can be advantageous, for example, when the dressing body 102 employs a weaker, gentler or less aggressive skin-contact adhesive 115 on its second major surface 112 (e.g., a silicone-based or silicone-containing adhesive) that may not be particularly suitable for adhering to the medical article 60. In such embodiments, the flap 104 can include a stronger or more aggressive securing adhesive 117 (e.g., as compared to the skin-contact adhesive, such as an acrylate-based or acrylate-containing adhesive) that can be more suitable for adhering to the medical article 60 and/or the dressing body 102. Said another way, the adhesion between the second major surface 112 of the dressing body 102 and the skin (or skin surface) 50 is less than the adhesion between the second major surface 116 of the flap 104 and the first major surface 110 of the dressing body 102.

As a result, the recess 156 can allow a portion of the medical article 60 to pass therethrough to allow the skin-contact adhesive 115 to adhere to the patient's skin 50 (e.g., under the portion of the medical article 60, as shown in FIG. 1), while also allowing the flap 104 to secure the portion of the medical article 60 with the securing adhesive 117 to the first major surface 110 of the dressing body 102, adjacent the recess 156, without adhering the securing adhesive 117 to the patient's skin 50. As a result, the portion of the medical article 60 can be coupled (e.g., sandwiched) between the flap 104 and the dressing body 102. Furthermore, the free end 122 of the flap 104 can at least partially overlap or cover at least a portion of the recess 156 in the dressing body 102, when the free end 122 of the flap 104 is in the second position $P_2$, to inhibit movement (e.g., longitudinally, laterally and/or vertically) of the portion of the medical article 60 desired to be secured. That is, in embodiments employing a catheter system as the medical article 60, the insertion site 65, the output catheter 66, and at least a portion of the catheter hub 64 can be covered by the distal portion 106 of the dressing body 102 that is free of the flap 104, and at least the input catheter 62 can be secured using the flap 104.

Further details of the skin-contact adhesive 115 and the securing adhesive 117 are described in greater detail below.

Figure 11:
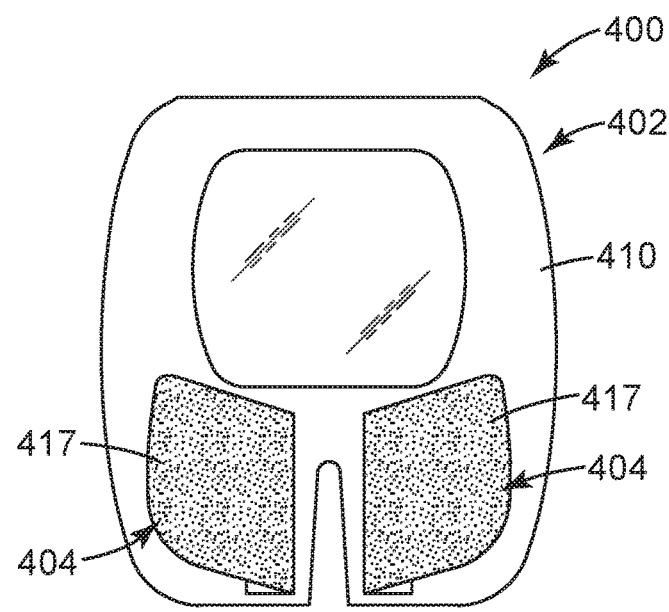
FIG. 11 is a top plan view of a medical dressing according to another embodiment of the present disclosure.
Figure 12:
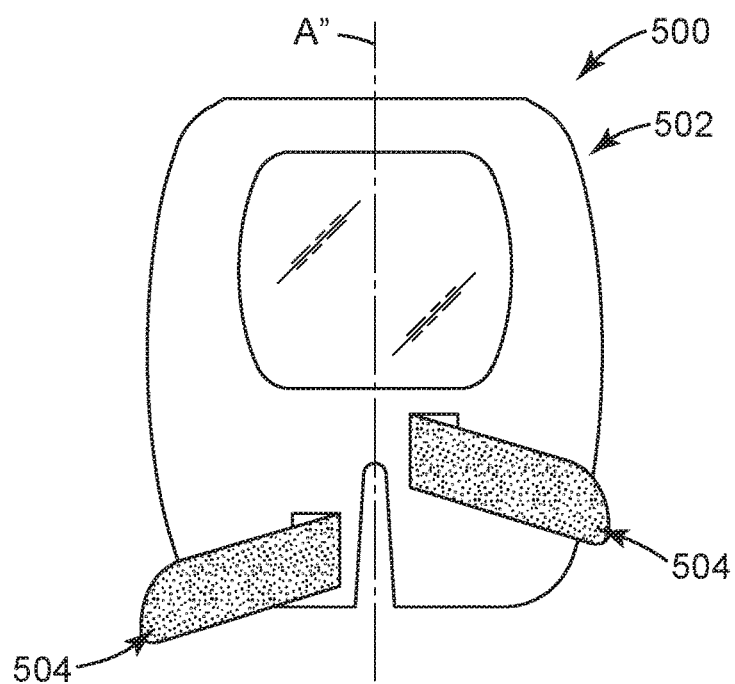
FIG. 12 is a top plan view of a medical dressing according to another embodiment of the present disclosure.
Figure 14:
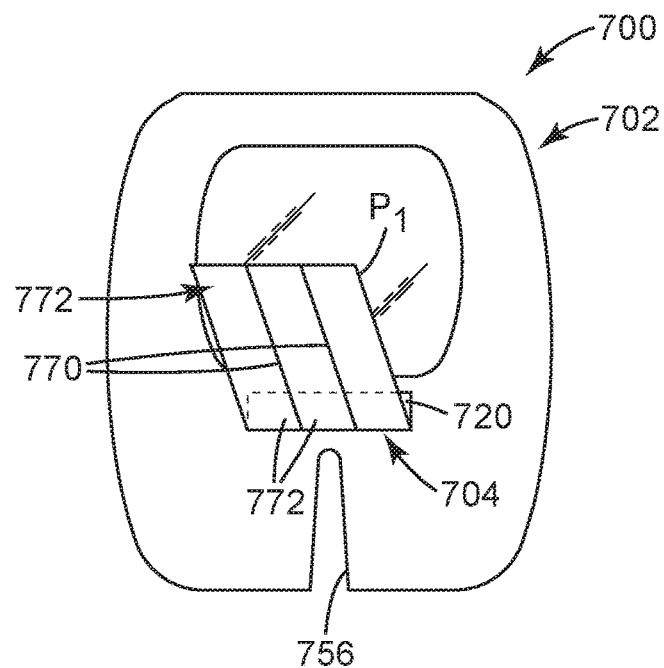
FIG. 14 is a top plan view of a medical dressing according to another embodiment of the present disclosure.

In some embodiments, e.g., as shown in FIGS. 11 and 12 and described below, the flap 104 can be one of a plurality of flaps 104 that can be oriented in parallel or in opposing fashion (e.g., hinging on opposite sides of the dressing body 102), or a combination thereof. In addition, even though the fixed end 120 of the flap 104 is illustrated as being located on a side of the dressing body 102 such that the flap 104 opens and closes sideways, it should be understood that the fixed end 120 (and the hinge 125) can be located anywhere on or adjacent the dressing body 102 to achieve a flap 104 that overlaps the proximal portion 108 of the dressing body 102, such that the distal portion 106 of the dressing body 102 remains free of the flap 104. For example, in some embodiments, as shown in FIG. 14 and described below, the fixed end 122 (and the hinge 125) of the flap 104 can be located just proximally of the transparent window 109 of the dressing body 102 and can flap down (or close) proximally to overlap the dressing body 102 and to move to the second position $P_2$. Furthermore, in some embodiments, the fixed end 122 (and the hinge 125) of the flap 104 can be located at or adjacent the proximal end 107 of the dressing body 102 such that the flap 104 can flap distally to overlap the dressing body 102 and to move to the second position $P_2$, i.e., while still allowing the distal portion 106 of the dressing body 102 to remain free of the flap 104.

Figure 3:
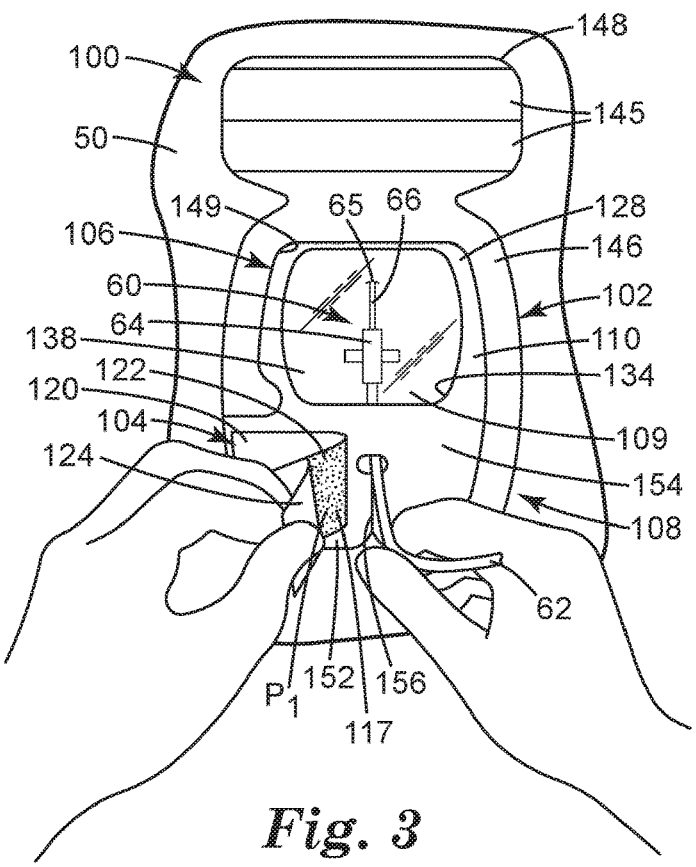
FIGS. 3-5 illustrate a method for coupling a medical article to a patient with the medical dressing of FIGS. 1-2.
Figure 4:
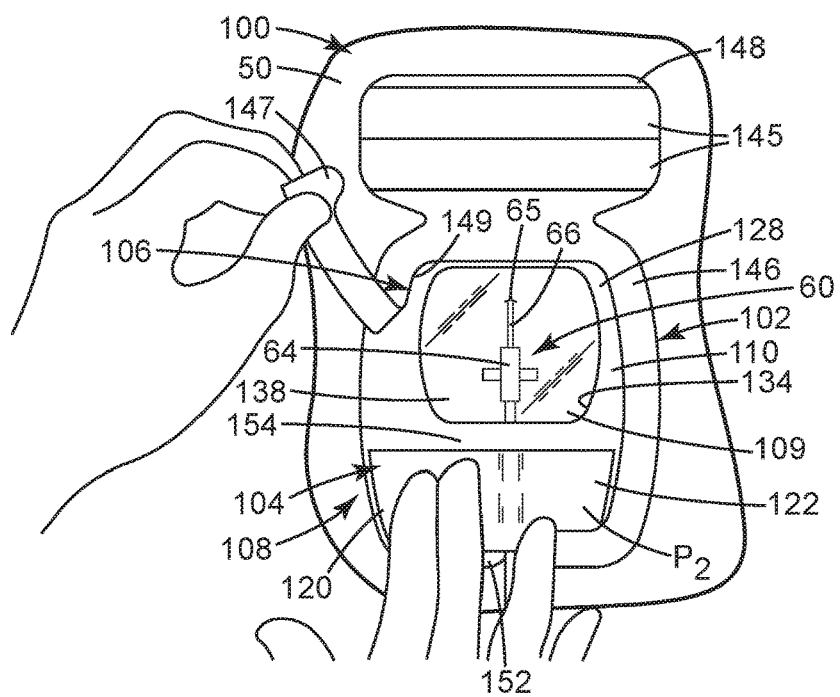
Figure 5:
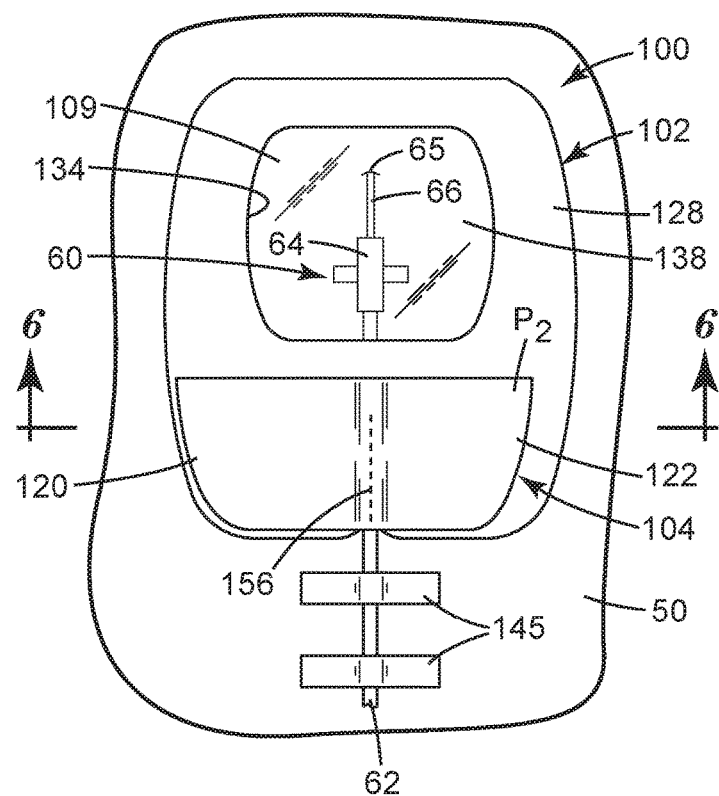
Figure 6:
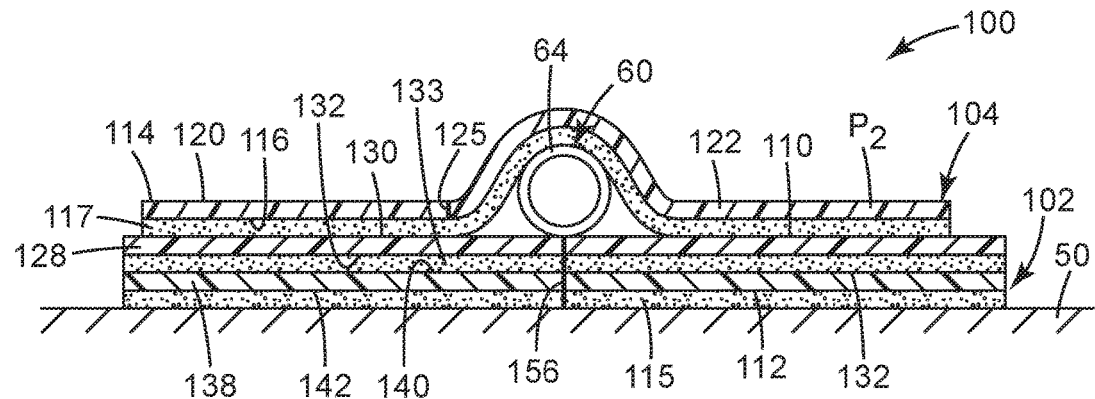
FIG. 6 is a cross-sectional view of the medical dressing of FIGS. 1-5, taken along line 6-6 of FIG. 5.

FIGS. 3-5 depict an exemplary method of applying the medical dressing 100 to a patient. In FIGS. 3-5, the medical dressing 100 is depicted as covering the medical article 60, wherein the medical article 60 is the above-described catheter system. The medical dressing 100 can be applied to a patient by first cleaning the application area of the skin 50 and inserting the output catheter 66 into the patient at the insertion site 65. The release liner can then removed from the medical dressing 100, exposing the second major surface 112 of the dressing body 102 (coated with the skin-contact adhesive 115). Once removed from release liner, the medical dressing 100 can be positioned on the skin 50 such that the transparent window 109 covers the insertion site 65, the distal portion 106 of the dressing body 102 covers the insertion site 65, the output catheter 66 and at least a portion of the catheter hub 64, and the proximal portion 108 of the dressing body 102 and the flap 104 covers at least a portion of the input catheter 62 and optionally a portion of the catheter hub 64, for example. The edges of the medical dressing 100 can then be gently and smoothly pressed against the patient's skin 50, thereby bringing the exposed skin-contact adhesive 115 in contact with the patient, as shown in FIG. 3. The catheter line 62 is pulled through the recess 156 to exit the dressing 102.

As shown in FIG. 3, the release liner 124 coupled to the second major surface 116 of the free end 122 of the flap 104 can be removed to expose the securing adhesive 117 on the second major surface 116 of the flap 104. The free end 122 of the flap 104 can then be moved from the first position $P_1$ (FIG. 3) to the second position $P_2$ (FIG. 4) over at least a portion of the input catheter 62, the proximal portion 108 of the dressing body 102, and the recess 156, adhering the securing adhesive 117 to the first major surface 110 of the dressing body 102 and securing the medical article 60.

After the dressing body 102 and the flap 104 are properly in position and adhered to a patient's skin 50, the carrier layer 146 can be removed, as shown in FIG. 4. Generally, removal of the carrier layer 146 can be accomplished by grasping the carrier layer 146, e.g., at area 147 and using a peeling motion toward the edges of the medical dressing 100 to remove the carrier layer 146. After application of the medical dressing 100, the optional auxiliary tape strips 145 can be placed over portions of the dressing body 102 and/or over portions of the medical article 60, such as further proximal portions of the input catheter 62 that have exited the dressing body 102 via the recess 156, as shown in FIG. 5. The tape strips 145 can be provided with the medical dressing 100 as shown and described, or may be supplied separately.

The layers and materials discussed above are further described in detail below.

In some embodiments, an optional antimicrobial component may be included that is either separate from the medical dressing 100 or may be integral with the medical dressing 100. When employed, the antimicrobial component can be placed near or adjacent to the insertion site 65 of the medical article 60 to inhibit microbial growth in and around the insertion site 65. The antimicrobial component can include an absorbent foam or gel, such as used in a 3M® TEGADERM® CHG I.V. Securement Dressing, available from 3M Company.

Dressing Body and Flap

Suitable dressings for the dressing body 102 can include, but are not limited to, one or more of a fabric, a woven fibrous web, a nonwoven fibrous web, a knit, a polymeric film, other familiar dressing materials, or combinations thereof. The dressing materials (e.g., for the base layer 138) can be translucent or transparent polymeric elastic films, and can include, but are not limited to, films formed of elastomeric polyurethanes, co-polyesters, polyethylenes, or combinations thereof. The dressing body 102 (e.g., the base layer 138 in the embodiment of FIGS. 1-6) can be a high moisture vapor permeable film. U.S. Pat. No. 3,645,835 describes methods of making such films and methods for testing their permeability.

The dressing body 102 advantageously should transmit moisture vapor at a rate equal to or greater than human skin. In some embodiments, the adhesive-coated dressing body 102 can transmit moisture vapor at a rate of at least 300 g/m$^2$/24 hrs/37° C./100-10% RH, and in some embodiments, at least 700 g/m$^2$/24 hrs/37° C./100-10% RH. The dressing body 102 is generally conformable to anatomical surfaces. As such, when the dressing body 102 is applied to an anatomical surface, it conforms to the surface even when the surface is moved. The dressing body 102 can also be conformable to animal anatomical joints. When the joint is flexed and then returned to its unflexed position, the dressing body 102 can be made such that it stretches to accommodate the flexion of the joint, but is resilient enough to continue to conform to the joint when the joint is returned to its unflexed condition.

As mentioned above, the dressing body 102 can be a single layer of material or may be comprised of two or more layers, such as the top layer 128 and the base layer 138. The dressing body 102 can be a flexible material. For example, the dressing body 102, or a portion thereof (e.g., the top layer 128 or the base layer 138, or both) may be a film, paper, woven, knitted, or nonwoven material or a combination of one or more layers of film, paper, woven, knitted, or nonwoven. In some embodiments, a transparent material for at least one of the top layer 128 and the base layer 138 can be desirable to allow for viewing of the underlying skin or medical device.

To add strength to a very thin film, all or a portion of the film may include an additional layer of another film, woven, knitted, or nonwoven fabric. For example, a 3M® TEGADERM® I.V. Advanced Dressing, available from 3M Company, includes a portion of the dressing which additionally includes a nonwoven substrate secured to a thin, transparent film.

In embodiments employing the top layer 128 and the base layer 138 (and optionally, additional layers), the top layer 128 and the base layer 138 can be formed of any of the materials described above. By way of example only, in some embodiments, the top layer 128 can be formed of a nonwoven available under the trade designation SONTARA® from DuPont Corporation, Wilmington, Del. and the securing adhesive 133, and the base layer 138 can be formed of a film available under the trade designation TEGADERM® from 3M Company, St. Paul, Minn. As described above, in some embodiments, the top layer 128 can actually be positioned underneath the base layer 138.

The flap 104 can be formed of any of the materials described above with respect to the dressing body 102.

Carrier Layer

The material used to form the carrier layer 146 is generally substantially more rigid than the dressing body 102 to prevent the dressing body 102 from improperly wrinkling during application to a patient. The carrier layer 146 can be heat-sealable to the dressing body 102 with or without a low adhesion coating described above. In general, the carrier layer materials can include, but are not limited to, polyethylene/vinyl acetate copolymer-coated papers and polyester films. One example of a suitable carrier layer material is a polyethylene/vinyl acetate copolymer coated super calendared Kraft paper (1-80BKG-157 PE; LOPAREX of Willowbrook, Ill.).

The carrier layer 146 can include perforations to aid in separating portions of the carrier layer 146 after application of the medical dressing 100 to a patient. Spacing and shape of the perforations are adjusted to give a carrier layer with relatively easy to tear performance on removal of the carrier layer from the applied dressing. The perforations may be shaped in accordance with any of the accepted perforation patterns including linear, angled, Y-shaped, V-shaped, dual-angled offset, sinusoidal, etc.

Release Liner

Release liners suitable for use with the medical dressings of the present disclosure can be made of can include, but are not limited to, kraft papers, polyethylene, polypropylene, polyester, or combinations thereof. Such liners can be coated with release agents, such as fluorochemicals, silicones, or other suitable low surface energy materials. Other adhesives and release liner combinations known to those of ordinary skill in the art can also be employed in the medical dressings of the present disclosure. Examples of commercially available silicone coated release papers are POLYSLIK™, silicone release papers available from Rexam Release (Bedford Park, Ill.) and silicone release papers supplied by LOPAREX (Willowbrook, Ill.). Other non-limiting examples of such release liners commercially available include siliconized polyethylene terephthalate films, commercially available from H. P. Smith Co., and fluoropolymer coated polyester films, commercially available from 3M Company (St. Paul) under the brand "SCOTCHPAK™" release liners.

Adhesives

As described above, the securing adhesives 117 and 133 can have an adhesion that is higher than the skin-contact adhesive 115. In some embodiments, the securing adhesive 117, 133 and the skin-contact adhesive 115 may be of the same or similar classes of adhesive, but have different adhesion levels. For example, the securing adhesive 117, 133 and/or the skin-contact adhesive 115 may be an acrylate, silicone, urethane, hydrogel, hydrocolloid, natural rubber, or synthetic rubber. Adhesion can also be tuned through changes in adhesive composition, adhesive thickness, or adhesive surface area (e.g., by employing a pattern-coated adhesive).

"Adhesion" refers to the force required to separate an adhesive from an underlying substrate. Adhesion can be measured in a number of ways. For example, adhesion can be defined by peel force or shear force. In some embodiments, adhesion can be defined by peel adhesion using ASTM D3330/D3330M-04(2010). In some embodiments, adhesion can be defined by shear adhesion using ASTM D3654M-06(2011). Adhesion is highly dependent on the specific substrate being adhered to, as well as the time the pressure-sensitive adhesive (PSA) is allowed to dwell on the substrate.

For example, typical peel adhesion values exhibited by pressure-sensitive adhesives in medical dressings maybe in the range of 20 to 300 g/cm as measured from stainless steel. In some embodiments, at least 10% higher peel adhesion, as measured by ASTM D3330/D3330M-04(2010), of the securing adhesive 117, 133 over the skin-contact adhesive 115 may realize the benefit of both securing to the medical article 60, while providing gentle adhesion to the skin 50.

In some embodiments, the securing adhesive 117, 133 can be an acrylate adhesive and the skin-contact adhesive 115 can be a silicone adhesive. The term "acrylate" or "acrylate-based" or "acrylate-containing" refers to monomeric acrylic or methacrylic esters of alcohols. Acrylate and methacrylate monomers are referred to collectively herein as "acrylate" monomers. Materials that are described as "acrylate-based" or "acrylate-containing" contain at least some acrylate monomers and may contain additional co-monomers.

Acrylate adhesives are well suited for securing adhesive dressings to medical articles, or skin. The adhesion can be manipulated to have high adhesion or low adhesion. Generally, the adhesion between acrylate adhesives and another material will increase over time. This property makes acrylate adhesives well suited as the securing adhesive 117, 133, which is intended to secure the medical article 60.

Suitable acrylate adhesives that can be applied to skin such as the acrylate copolymers are described in U.S. Pat. No. RE 24,906, the disclosure of which is hereby incorporated by reference. In particular, a 97:3 iso-octyl acrylate:acrylamide copolymer. Another acrylate adhesive is an 70:15:15 isooctyl acrylate:ethyleneoxide acrylate:acrylic acid terpolymer, as described in U.S. Pat. No. 4,737,410 (Example 31), the disclosure of which is hereby incorporated by reference. Other useful acrylate adhesives are described in U.S. Pat. Nos. 3,389,827, 4,112,213, 4,310,509, and 4,323,557, the disclosures of which are incorporated herein by reference.

The term "silicone" or "silicone-based" or "silicone-containing" refers to polymers that contain units with dialkyl or diaryl siloxane ($-SiR_2O-$) repeating units. The silicone-based polymers may be segmented copolymers or polysiloxanes polymers. The terms silicone and siloxane are used interchangeably.

Generally, silicone adhesives are able to effectively secure dressings and tape to skin and upon removal from the skin produce little or no skin damage. Typically, silicone adhesives do not adhere well to polymer-based substrates, like tubing or hardgoods, for example that are often present in medical articles. Thus lack of strong adhesion to medical devices/tubing combined with the gentle removal of silicone adhesives from skin make these adhesives well suited as the skin-contact adhesive 115.

Examples of suitable silicone adhesive systems can include, but are not limited to, products available under the following trade designations: Dow Corning MG 7-9850, Wacker SILPURAN® 2110 and 2130, Bluestar SILBIONE® RT Gel 4317 and 4320, Nusil MED-6345 and 6350. Other examples of suitable silicone adhesives are disclosed in PCT Publications WO2010/056541, WO2010/056543 and WO2010/056544, the disclosures of which are incorporated herein by reference.

For skin-contact adhesives, it is desirable that the adhesive is able to transmit moisture vapor at a rate greater to or equal to that of human skin. While such a characteristic can be achieved through the selection of an appropriate adhesive, it is also contemplated that other methods of achieving a high relative rate of moisture vapor transmission may be used, such as perforating the adhesive or pattern coating the adhesive, as described in U.S. Pat. No. 4,595,001 and U.S. Pat. App. Pub. 2008-0233348, the disclosures of which are incorporated herein by reference. Each of the securing or skin-contact adhesive can optionally be applied in a discontinuous manner.

Additional exemplary embodiments of medical dressings of the present disclosure will now be described with respect to FIGS. 7-14. FIGS. 7-14 illustrate various medical dressings of the present disclosure, wherein like numerals represent like elements. The medical dressings of FIGS. 7-14 share many of the same elements, features, and functions as the medical dressing 100 described above with respect to FIGS. 1-6. Reference is made to the description above accompanying FIGS. 1-6 for a more complete description of the features and elements (and alternatives to such features and elements) of the embodiments illustrated in FIGS. 7-14. Any of the features described above with respect to FIGS. 1-6 can be applied to the embodiments of FIGS. 7-14, and vice versa. The same medical article 60 illustrated in FIGS. 1 and 3-6 as being coupled to the medical dressing 100 can also be used with each of the medical dressings of FIGS. 7-14 and will be described with respect to each of FIGS. 7-14 by way of example only.

FIGS. 7-8 illustrate a medical dressing 200 according to another embodiment of the present disclosure. The medical dressing 200 includes a dressing body 202 having a distal end 205, a distal portion 206, a top layer 228, a base layer 238, a transparent window 209 in the distal portion 206, a proximal end 207, a proximal portion 208, a first major surface 210 (e.g., defined by the top layer 228), a second major surface 212 (e.g., defined by the base layer 238) comprising a skin-contact adhesive 215; and a recess 256. The medical dressing 200 further includes a flap 204 integrally formed with the dressing body 202 and comprising a fixed end 220 coupled to the dressing body 202 and separated from the remainder of the dressing body 202 by a living hinge 225, a free end 222, a first major surface 214 (see FIG. 8), a second major surface 216 comprising a securing adhesive 217, and a release liner 224 coupled to the second major surface 216, i.e., prior to use. FIG. 7 illustrates the flap 204 in a first (open) position $P_1$ with the release liner 224, and FIG. 8 illustrates the flap 204 in a second (closed) position $P_2$, where it is further shown as securing the medical article 60 between the flap 204 and the first major surface 210 of the dressing body 202.

The medical dressing 200 includes many similarities with the medical dressing 100 of FIGS. 1-6, except that the medical dressing 200 of FIGS. 7-8, except that the fixed end 220 of the flap 204 is integrally formed with the dressing body 202 and is separated from the dressing body 202 by a living hinge 225. By way of example only, the flap 204 of the embodiment of FIGS. 7-8 is formed only of the top layer 228 of the dressing body 202 and not the base layer 238; however, it should be understood that the flap 204 can be formed of the top layer 228, the base layer 238, or both.

Figure 9:
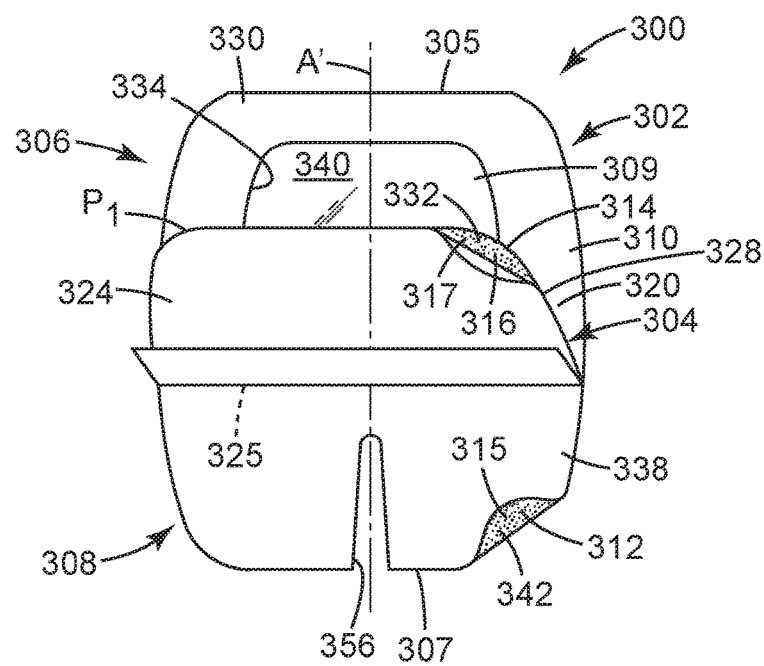
FIG. 9 is a top plan view of a medical dressing according to another embodiment of the present disclosure.
Figure 10:
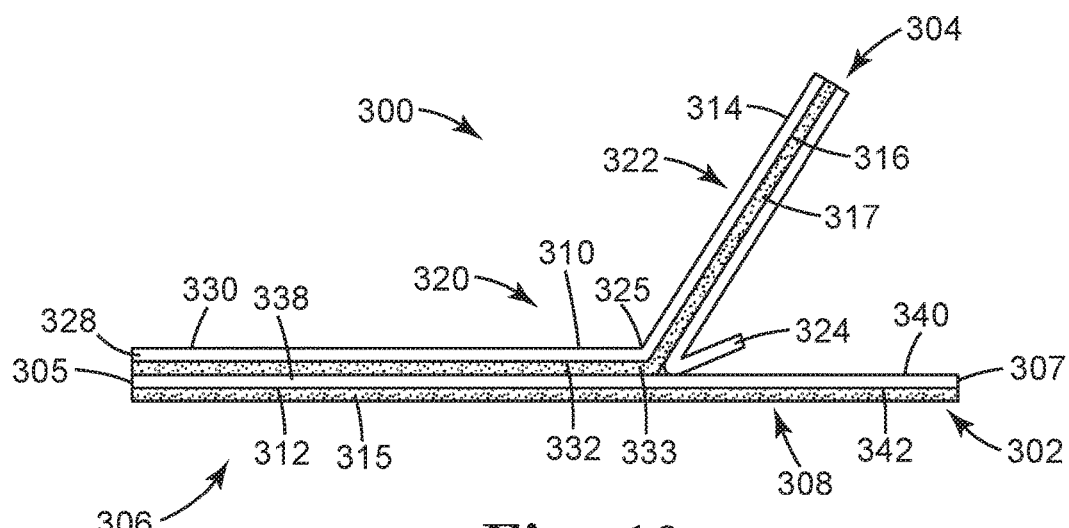
FIG. 10 is a side view of the medical dressing of FIG. 9.

FIGS. 9-10 illustrate a medical dressing 300 according to another embodiment of the present disclosure. The medical dressing 300 includes a dressing body 302. The dressing body 302 includes a top layer 328, a bottom layer 338, a distal end 305, a distal portion 306, a transparent window 309 in the distal portion 306, a proximal end 307, a proximal portion 308, a first major surface 310, a second major surface 312 comprising a skin-contact adhesive 315; and a recess 356. The medical dressing 300 includes many similarities with the medical dressing 100 of FIGS. 1-6, except that in the medical dressing 300 of FIGS. 9-10 the top layer 328 of the dressing body 302 (and particularly, in the proximal portion 308 of the dressing body 302) forms the flap 304, such that the flap 304 is integrally formed with at least a portion (i.e., the top layer 328) of the dressing body 302, and is separated from the remainder of the dressing body 302 (i.e., the remainder (distal portion 306) of the top layer 328 of the dressing body 302) by a living hinge 325. As shown, the living hinge 325 can be positioned to extend transversely with respect to a longitudinal axis A' (see FIG. 9) of the dressing body 302, separating the distal portion 306 of the top layer 328 from the proximal portion 308.

The top layer 328 of the dressing body 302, and particularly, the distal portion 306 thereof, serves as a fixed end 320 of the flap 304 that is coupled to the dressing body 302. The proximal portion 308 of the top layer 328 serves as a free end 322 of the flap 304. The top layer 328 further includes an opening 334 (FIG. 9) defining the transparent window 309. Thus, no portion of the flap 304 interferes with visualizing a distal portion of a medical article, and the movable free end 322 of the flap 304 is still located toward the proximal end 307 of the dressing body 302, such that the distal portion 306 of the dressing body 302 is still "free of the flap" 304.

The flap 304 (or at least the free end 322 of the flap 304) further includes a first major surface 314, a second major surface 316 comprising a securing adhesive 317, and a release liner 324 coupled to the second major surface 316, i.e., prior to use. The flap 304 is illustrated in a first (open) position $P_1$ in FIGS. 9 and 10, but the flap 304 is movable to a second (closed) position to secure a medical article between the top layer 328 (i.e., the free end 322 of the flap 304) and the base layer 338 of the dressing body 302 and to overlap the proximal portion 308 of the base layer 338 and at least a portion of the recess 356. The recess 356 can be used as described above to allow the portion of the medical article that is to be secured by the flap 304 to be located between the flap 304 and the base layer 338 of the dressing body 302.

The top layer 328 (or the fixed end 320 of the flap 304) can include a first major surface 330 and a second major surface 332 opposite the first major surface 330 and including a securing adhesive 333. The base layer 338 can include a first major surface 340 and a second major surface 342. The second major surface 332 of the top layer 328 is positioned to be coupled to the first major surface 340 of the base layer 338, and the second major surface 342 of the base layer 338 is configured to be coupled to skin. As a result, the first major surface 330 of the top layer 328 can correspond to the overall first major surface 310 of the dressing body 302, and the second major surface 342 of the base layer 338 can correspond to the overall second major surface 312 of the dressing body and can include the skin-contact adhesive 315. By way of example only, the second major surface 342 of the base layer 328 can include a silicone-based or a silicone-containing adhesive and the second major surface 332 of the top layer 328 can include an acrylate-based or a an acrylate-containing adhesive.

FIG. 11 illustrates a medical dressing 400 according to another embodiment of the present disclosure. The medical dressing 400 includes a dressing body 402 and two flaps 404 that oppose one another and can function together to a secure a medical article. The two opposing flaps 404 can be configured to couple to one another (e.g., via a securing adhesive 417) and/or to a first major surface 410 of the dressing body 402.

FIG. 12 illustrates a medical dressing 500 according to another embodiment of the present disclosure. The medical dressing 500 includes a dressing body 502 and two or more flaps 504 that oppose one another and are spaced longitudinally apart from one another along a longitudinal axis A" of the dressing body 502, such that one flap 504 is located further distally than another (or one is located more proximally than another), and such that the multiple flaps 504 can be used to secure different portions of a medical article, for example, along its length.

Figure 13:
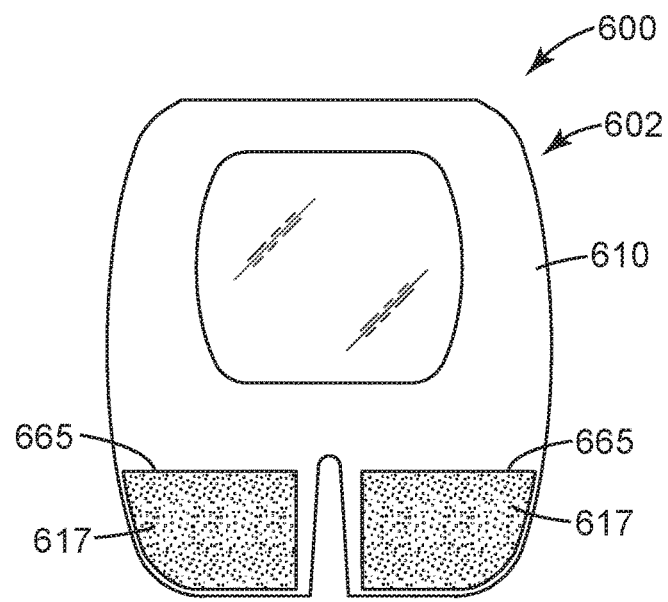
FIG. 13 is a top plan view of a medical dressing according to another embodiment of the present disclosure.

FIG. 13 illustrates a medical dressing 600 according to another embodiment of the present disclosure. The medical dressing 600 includes a dressing body 602 and is an example of an embodiment in which a securing adhesive 617 for a flap (not shown, but any of the above-described flaps can be employed) can be provided by one or more adhesive landing pads 665 located on a first major surface 610 of the dressing body 602. In some embodiments, one or more adhesive landing pads 665 can be used to secure the free end of a flap, and in some embodiments, the adhesive landing pads 665 can be used to secure both the fixed end and the free end of a flap of the present disclosure.

FIG. 14 illustrates a medical dressing 700 according to another embodiment of the present disclosure. The medical dressing 700 includes a dressing body 702 and a flap 704. The flap 704 includes one or more slits, notches or cutaway regions 770 that separate the flap 704 into multiple portions or sections 772, e.g., which can be wrapped around a medical article (e.g., catheter tubing). By way of example only, the flap 704 includes a fixed end 720 that is coupled to the dressing body 702 at a location that is proximal with respect to a transparent window 709 of the dressing body 702, and wherein a free end 722 of the flap 704 flaps proximally from its first position $P_1$ to the second position (not shown) where the flap 704 overlaps at least a portion of the dressing body 702 and, particularly, a recess 756 in the dressing body 702.

Each embodiment shown in the figures is illustrated as a separate embodiment for clarity in illustrating a variety of features of the medical dressings of the present disclosure. However, it should be understood that any combination of elements and features of any of the embodiments illustrated in the figures and described herein can be employed in the medical dressings of the present disclosure.

EMBODIMENTS

Embodiment 1 is a medical dressing, e.g., for securing a medical article to a skin surface, the medical dressing comprising:
  a dressing body comprising
    a first major surface,
    a second major surface, opposite the first major surface; and
  a flap comprising a first major surface,
a second major surface, opposite the first major surface, comprising a securing adhesive,
a fixed end coupled to the dressing body, and
a free end movable with respect to the dressing body between a first position in which the free end is not positioned in an overlapping relationship with the dressing body and a second position in which the free end is positioned in overlapping relationship with the dressing body;
wherein the second major surface of at least the free end of the flap is configured to be secured to the dressing body; and
wherein the flap is located toward a proximal end of the dressing body, such that a distal portion of the dressing body is free of the flap.

Embodiment 2 is the medical dressing of embodiment 1, wherein the second major surface of at least the free end of the flap is configured to be secured to the dressing body by a securing adhesive.

Embodiment 3 is the medical dressing of embodiment 2, wherein the fixed end of the flap is secured to the first major surface of the dressing body with the securing adhesive.

Embodiment 4 is the medical dressing of embodiment 2 or 3, wherein a first portion of the second major surface of the flap is secured by the securing adhesive to the first major surface of the dressing body, and wherein a second portion of the second major surface of the flap includes a removable release liner covering the securing adhesive.

Embodiment 5 is the medical dressing of any of embodiments 1-4, wherein the fixed end of the flap is integrally formed with the dressing body.

Embodiment 6 is the medical dressing of embodiment 5, wherein the fixed end of the flap is separated from the dressing body by a living hinge.

Embodiment 7 is the medical dressing of any of embodiments 1-6, wherein the skin-contact adhesive comprises a silicone adhesive.

Embodiment 8 is the medical dressing of any of embodiments 2-7, wherein the securing adhesive comprises an acrylate adhesive.

Embodiment 9 is the medical dressing of any of embodiments 2-8, wherein the adhesion between the second major surface of the dressing body and the skin surface is less than the adhesion between the second major surface of the flap and the first major surface of the dressing body.

Embodiment 10 is the medical dressing of any of embodiments 2-9, wherein the skin-contact adhesive has a lower adhesion than the securing adhesive.

Embodiment 11 is the medical dressing of any of embodiments 1-10, wherein the dressing body further comprises:
a perimeter surrounding a central portion of the dressing body, and
a recess extending from the perimeter into a central portion of the dressing body.

Embodiment 12 is the medical dressing of embodiment 11, wherein the free end of the flap overlaps at least a portion of the recess in the dressing body when the free end of the flap is in the second position.

Embodiment 13 is the medical dressing of embodiment 11 or 12, wherein the recess is configured to allow a portion of the medical article to extend from the second major surface of the dressing body to the first major surface of the dressing body.

Embodiment 14 is the medical dressing of embodiment 13, wherein the flap is positioned to secure the portion of the medical article to the first major surface of the dressing body, adjacent the recess in the dressing body.

Embodiment 15 is the medical dressing of embodiment 13 or 14, wherein the medical article includes a catheter system comprising a catheter, and wherein the portion of the medical article includes a proximal portion of the catheter, located proximally with respect to an insertion site.

Embodiment 16 is the medical dressing of embodiment 15, wherein the insertion site is covered by a distal portion of the dressing body that is free of the flap.

Embodiment 17 is the medical dressing of any of embodiments 11-16, wherein the recess is formed in a proximal portion of the dressing body.

Embodiment 18 is the medical dressing of any of embodiments 11-17, wherein the recess extends through a proximal end of the dressing body.

Embodiment 19 is the medical dressing of any of embodiments 1-18, wherein the flap is positioned in overlapping relationship with a proximal portion of the dressing body when the free end of the flap is in the second position.

Embodiment 20 is the medical dressing of any of embodiments 1-19, wherein the flap is located toward a proximal end of the dressing body.

Embodiment 21 is the medical dressing of any of embodiments 2-20, wherein a removable release liner covers at least a portion of the securing adhesive on the second major surface of the flap.

Embodiment 22 is the medical dressing of any of embodiments 1-21, wherein the dressing body includes a transparent window, and wherein the flap is located proximally with respect to the transparent window.

Embodiment 23 is the medical dressing of any of embodiments 1-22, wherein the second major surface of the dressing body adjacent the recess includes the skin-contact adhesive.

Embodiment 24 is the medical dressing of any of embodiments 1-23, wherein the flap is formed by a portion of the dressing body.

Embodiment 25 is the medical dressing of embodiment 24, wherein the dressing body includes a base layer and a top layer, and wherein the flap is formed by the top layer of the dressing body to secure at least a portion of the medical article between the top layer and the base layer of the dressing body.

Embodiment 26 is the medical dressing of embodiment 24 or 25, wherein a second major surface of the top layer is positioned to be coupled to a first major surface of the base layer, wherein a second major surface of the base layer is configured to be coupled to skin, and wherein the second major surface of the base layer includes a silicone adhesive and the second major surface of the top layer includes an acrylate adhesive.

Embodiment 27 is the medical dressing of embodiment 25 or 26, wherein the flap is separated from a remainder of the top layer by a living hinge.

Embodiment 28 is the medical dressing of embodiment 27, wherein the living hinge is positioned to extend transversely with respect to a longitudinal axis of the dressing body, separating a distal portion of the top layer from a proximal portion.

Embodiment 29 is the medical dressing of any of embodiments 1-28, wherein the flap is one of a plurality of flaps that oppose one another.

Embodiment 30 is the medical dressing of any of embodiments 2-29, wherein the second major surface of at least the free end of the flap comprises the securing adhesive.

Embodiment 31 is the medical dressing of any of embodiments 2-30, wherein the securing adhesive is provided by at least one adhesive landing pad on the first major surface of the dressing body.

Embodiment 32 is the medical dressing of any of embodiments 1-31, wherein the flap includes at least one slit to separate the flap into multiple portions.

Embodiment 33 is the medical dressing of any of embodiments 1-32, wherein the fixed end of the flap is coupled to the dressing body at a location that is proximal with respect to a transparent window of the dressing body, and wherein the free end of the flap is moves proximally from the first position to the second position.

Embodiment 34 is a medical dressing comprising:
  a dressing body comprising
    a first major surface, and
    a second major surface, opposite the first major surface, wherein at least a portion of the second major surface comprises a silicone adhesive; and
  a flap comprising
    a first major surface,
    a second major surface, opposite the first major surface,
    a fixed end coupled to the dressing body, and
    a free end movable with respect to the dressing body between an open position in which the free end is not positioned in an overlapping relationship with the dressing body and a second position in which the free end is positioned in overlapping relationship with the dressing body;
  wherein at least the free end of the flap is configured to be secured to the dressing body by an acrylate adhesive when the free end of the flap is in the second position.

Embodiment 35 is the medical dressing of embodiment 34, wherein a removable release liner covers at least a portion of the acrylate adhesive on the second major surface of the flap.

Embodiment 36 is the medical dressing of embodiment 34 or 35, wherein the fixed end of the flap is integrally formed with the dressing body.

Embodiment 37 is the medical dressing of embodiment 36, wherein the fixed end of the flap is separated from the dressing body by a living hinge.

Embodiment 38 is the medical dressing of any of embodiments 34-37, wherein the second major surface of the fixed end of the flap is secured to the first major surface of the dressing body by the acrylate adhesive.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. A medical dressing comprising:
  a dressing body comprising
    a first major surface,
    a second major surface, opposite the first major surface, comprising a skin-contact adhesive; and
  a flap comprising
    a first major surface,
    a second major surface, opposite the first major surface,
    a fixed end coupled to the dressing body, and
    a free end movable with respect to the dressing body between a first position in which the free end is not positioned in an overlapping relationship with the dressing body and a second position in which the free end is positioned in overlapping relationship with the dressing body,
  wherein the second major surface of at least the free end of the flap is configured to be secured to the dressing body, wherein the flap is located toward a proximal end of the dressing body, such that a distal portion of the dressing body is free of the flap, wherein the second major surface of at least the free end of the flap is configured to be secured to the dressing body by a securing adhesive, and wherein the adhesion between the second major surface of the dressing body and the skin surface is less than the adhesion between the second major surface of the flap and the first major surface of the dressing body.

2. The medical dressing of claim 1, wherein the fixed end of the flap is secured to the first major surface of the dressing body with the securing adhesive.

3. The medical dressing of claim 1, wherein the skin-contact adhesive comprises a silicone adhesive, and wherein the securing adhesive comprises an acrylate adhesive.

4. The medical dressing of claim 1, wherein the dressing body further comprises:
  a perimeter surrounding a central portion of the dressing body, and
  a recess extending from the perimeter into a central portion of the dressing body.

5. The medical dressing of claim 4, wherein the free end of the flap overlaps at least a portion of the recess in the dressing body when the free end of the flap is in the second position.

6. The medical dressing of claim 4, wherein the recess is configured to allow a portion of the medical article to extend from the second major surface of the dressing body to the first major surface of the dressing body, and wherein the flap is positioned to secure the portion of the medical article to the first major surface of the dressing body, adjacent the recess in the dressing body.

7. The medical dressing of claim 6, wherein the medical article includes a catheter system comprising a catheter, and wherein the portion of the medical article includes a proximal portion of the catheter, located proximally with respect to an insertion site.

8. The medical dressing of claim 7, wherein the insertion site is covered by a distal portion of the dressing body that is free of the flap.

9. The medical dressing of claim 1, wherein the dressing body includes a transparent window, and wherein the flap is located proximally with respect to the transparent window.

10. The medical dressing of claim 1, wherein the second major surface of at least the free end of the flap comprises the securing adhesive.

11. The medical dressing of claim 1, wherein the securing adhesive is provided by at least one adhesive landing pad on the first major surface of the dressing body.

12. The medical dressing of claim 1, wherein the fixed end of the flap is coupled to the dressing body at a location that is proximal with respect to a transparent window of the dressing body, and wherein the free end of the flap moves proximally from the first position to the second position.

* * * * *